US008445543B2

(12) United States Patent
Abou-Chacra Vernet et al.

(10) Patent No.: US 8,445,543 B2
(45) Date of Patent: *May 21, 2013

(54) COMBINATIONS OF ADAPALENE AND BENZOYL PEROXIDE FOR TREATING ACNE LESIONS

(75) Inventors: Marie-line Abou-Chacra Vernet, Nice (FR); Denis Gross, Callian (FR); Christian Loesche, Valbonne (FR); Michel Poncet, Mougins (FR)

(73) Assignee: Galderma Research & Development, Biot (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/308,413

(22) Filed: Nov. 30, 2011

(65) Prior Publication Data

US 2012/0136059 A1    May 31, 2012

Related U.S. Application Data

(63) Continuation of application No. 12/473,981, filed on May 28, 2009, now Pat. No. 8,080,537, which is a continuation-in-part of application No. 12/318,937, filed on Jan. 13, 2009, now Pat. No. 8,071,644, which is a continuation of application No. PCT/EP2007/057207, filed on Jul. 12, 2007.

(60) Provisional application No. 60/833,491, filed on Jul. 27, 2006.

(30) Foreign Application Priority Data

Jul. 13, 2006    (FR) ...................... 06 52968

(51) Int. Cl.
*A01N 31/04* (2006.01)
*A01N 31/00* (2006.01)
*A61K 31/07* (2006.01)
*A61K 31/075* (2006.01)

(52) U.S. Cl.
USPC .......................................... 514/725; 514/714

(58) Field of Classification Search
None
See application file for complete search history.

(56) References Cited

U.S. PATENT DOCUMENTS

| | | | |
|---|---|---|---|
| 5,733,886 A | 3/1998 | Baroody et al. | |
| 6,559,189 B2 | 5/2003 | Baker et al. | |
| 2003/0170196 A1 | 9/2003 | Orsoni et al. | |
| 2004/0157766 A1* | 8/2004 | Embil et al. | 514/1 |
| 2005/0148495 A1 | 7/2005 | Lambert et al. | |
| 2005/0239723 A1 | 10/2005 | Amin et al. | |
| 2006/0128808 A1 | 6/2006 | Arsonnaud et al. | |
| 2009/0191245 A1 | 7/2009 | Fredon et al. | |

FOREIGN PATENT DOCUMENTS

| | | |
|---|---|---|
| FR | 2 833 841 | 6/2003 |
| WO | 2006/045640 A1 | 5/2006 |
| WO | WO 2007/002831 A2 | 1/2007 |
| WO | 2007/132134 A1 | 11/2007 |

OTHER PUBLICATIONS

Daniele Caron Ph. D et al. "Skin Tolerance of Adapalene 0.1% Gel in Combination with other Topical Antiacne Treatments" *Journal of the American Academy of Dermatology* Jun. 1997 pp. S113-S115 vol. 36, No. 6 XP005177984.
B. Martin et al. "Chemical Stability of Adapalene and Tretinoin when Combined with Benzoyl Peroxide in Presence and in Absence of Visible Light and Ultraviolet Radiation" *British Journal of Dermatology* Oct. 1998 pp. 8-11 vol. 139 No. Suppl. 52 XP008007635.
C. Korkut et al. "Benzoyl Peroxide, Adapalene, and their Combination in the Treatment of Acne Vulgaris" *The Journal of Dermatology* 2005 vol. 32 No. 3 pp. 169-173 XP009075640.
Jonathan S. Weiss et al. "Adapalene for the Treatment of Acne Vulgaris" *Journal of the American Academy of Dermatology* Aug. 1998 vol. 39 No. 2 pp. S-50-S54 XP005177891.
"Evaluation of a Maintenance Treatment of Acne Vulgaris with Adapalene Gel 0.1%" *Journal of the American Academy of Dermatology* Mar. 2005 pp. 18 vol. 52 No. 3 XP00484027.
R. Capizzi et al. "Skin Tolerability and Efficacy of Combination Therapy with Hydrogen Peroxide Stabilized Cream and Adapalene Gel in Comparison with Benzoyl Peroxide Cream and Adapalene Gel in Common Acne. A Randomized, Investigator-Masked, Controlled Trial" *British Journal of Dermatology* 2004 vol. 151 No. 2 pp. 481-484 XP008073258.
A. Clucas et al. "Adapalene 0.1% get has Low Skin Irritation Potential" *Journal of the European Academy of Dermatology and Venereology, Elsevier Science Publishers* Sep. 1998 vol. 11 pp. S275 XP004556097.
Joseph B. Bikowski "Clinical Experience Results with Clindamycin 1% Benzoyl Peroxide 5% Gel (Duac) as Monotherapy and in Combination" *Journal of Drugs in Dermatology* 2005 vol. 4 No. 2 pp. 164-171 XP009079917.
Barbara Brand et al. "Cumulative Irritancy Comparison of Adapalene gel 0.1% Versus other Retinoid Products when Applied in Combination with Topical Antimicrobial Agents" *Journal of American Academy of Dermatology* Sep. 2003 vol. 49 No. 3 pp. S227-S232 XP002422710.
"Clinical Efficacy and Safety of 5% Benzoyl Peroxide Gel Combined with 0.1% Adapalene Gel in the Treatment of Acne Vulgaris: A Multicenter, Randomised Study" *Database Biosis (Onlline)* Jun. 2003 vol. 36 No. 6 pp. 310-312 XP002422712.
S. Hurwitz "The Combined Effect of Vitamin a Acid and Benzoyl Peroxide in the Treatment of Acne" *Cutis, Excerpta Medica* 1976 vol. 17 No. 3 pp. 585-590 XP008007633.

(Continued)

*Primary Examiner* — James D Anderson
*Assistant Examiner* — Stephanie Springer
(74) *Attorney, Agent, or Firm* — Dentons US LLP

(57) ABSTRACT

Adapalene or a pharmaceutically acceptable salt thereof formulated into a pharmaceutical composition is useful for reducing the number of acne lesions, via daily topical application, in combination or in association with benzoyl peroxide (BPO); such treatment may be via administration of a pharmaceutical composition combining adapalene and BPO or by a concomitant application of two pharmaceutical compositions, one containing adapalene and the other containing BPO.

10 Claims, 12 Drawing Sheets

OTHER PUBLICATIONS

International Search Report for corresponding PCT/EP2007/057207 dated Sep. 24, 2007.
Official Action dated Dec. 29, 2009 for copending U.S. Appl. No. 11/826,364, filed Jul. 13, 2007 including PTO-892 and initialed Form PTO-1449 attached thereto.
Official Action dated Jul. 23, 2010 for copending U.S. Appl. No. 11/826,364, field Jul. 13, 2007.
Official Action dated Oct. 21, 2009 for copending U.S. Appl. No. 12/318,937, filed Jan. 13, 2009.
Official Action dated Sep. 1, 2010 for copending U.S. Appl. No. 12/318,937, filed Jan. 13, 2009.
LV do Nascimento et al., "Single-blind comparative clinical study of the efficacy and safety of benzoyl peroxide 4% gel (BID) and adapalene 0.1% Gel (QD) in the treatment of acne vulgaris for 11 weeks," Journal of Dermatological Treatment, 2003, pp. 166-171, vol. 14.
Official Action issued on Sep. 25, 2012, by the Japanese Patent Office in corresponding Japanese Patent Application No. 2009-518901, and an English language translation thereof (6 pages in Japanese and 6 pages in English) with an English language copy of the examined claims (3 pages).
Gollnick et al. "Evaluation of a Maintenance Treatment of Acne Vulgaris with Adapalene Gel 0.1%" *Journal of the American Academy of Dermatology* Mar. 2005 p. 18 vol. 52 No. 3.
A. Clucas et al. "Adapalene 0.1% gel has Low Skin Irritation Potential" *Journal of the European Academy of Dermatology and Venereology, Elsevier Science Publishers* Sep. 1998 vol. 11 p. S275.
Wen-Wen et al. "Clinical Efficacy and Safety of 5% Benzoyl Peroxide Gel Combined with 0.1% Adapalene Gel in the Treatment of Acne Vulgaris: A Multicenter, Randomised Study" *Database Biosis (Online)* Jun. 2003 vol. 36 No. 6 pp. 310-312.
Leyden "A Review of the Use of Combination Therapies for the Treatment of Acne Vulgaris," *Journal of the American Academy of Dermatology*, vol. 49, No. 3, pp. S200-S210 (Sep. 2003).
Capizzi et al. "Efficacy and Safety of Combination Therapy of Hydrogen Peroxide Cream and Adapalene Gel in Comparison with Benzoyl Peroxide Cream and Adapalene in Common Acne," *Journal of the American Academy of Dermatology*, vol. 50, Issue 3, Supplement 1, p. 18 (Mar. 2004).
Office Action mailed Mar. 25, 2011 for U.S. Appl. No. 12/473,981, filed May 28, 2009.
Office Action mailed May 31, 2012 for U.S. Appl. No. 13/351,986, filed Jan. 17, 2012.
Office Action mailed Sep. 20, 2012 for U.S. Appl. No. 13/296,186, filed Nov. 14, 2011.
Extended European Search Report issued on Mar. 30, 2012, in corresponding European Patent Application No. 12 15 2317, Written Opinion and originally filed claims 1-10 of EP 12 15 2317 (14 pages).

\* cited by examiner

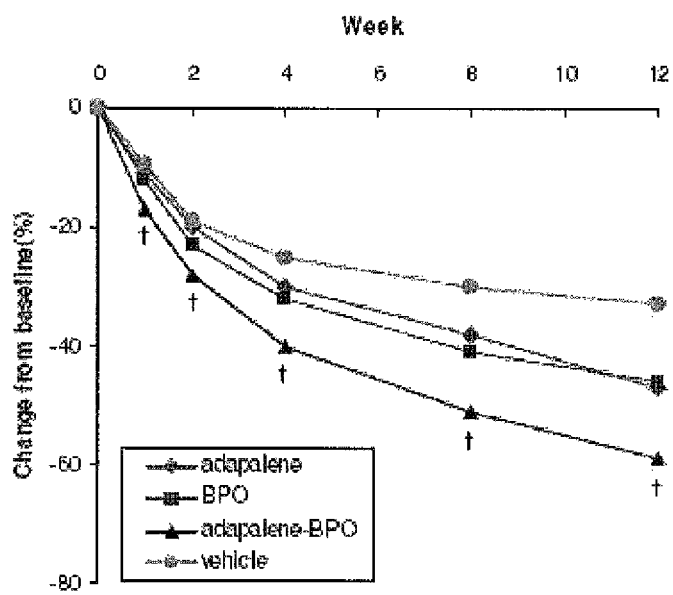
Figure 7A
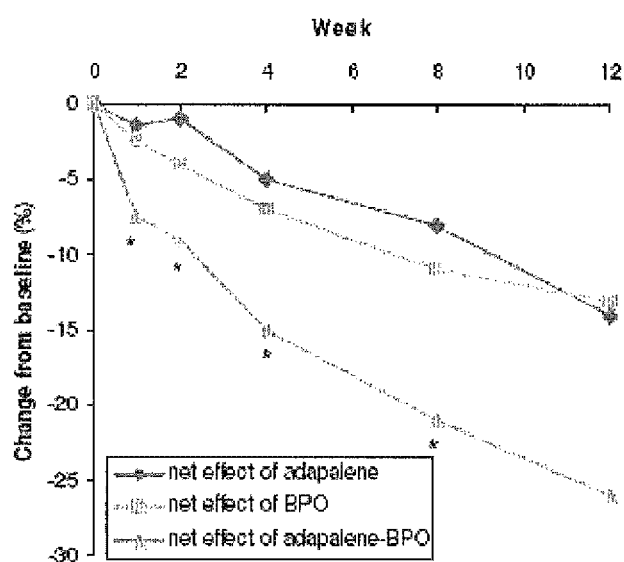
Figure 7B
| week | 1 | 2 | 4 | 8 |
|---|---|---|---|---|
| contribution of synergy to efficacy of adapalene-BPO | 48.7% | 44.4% | 20.0% | 9.5% |
Figure 7C

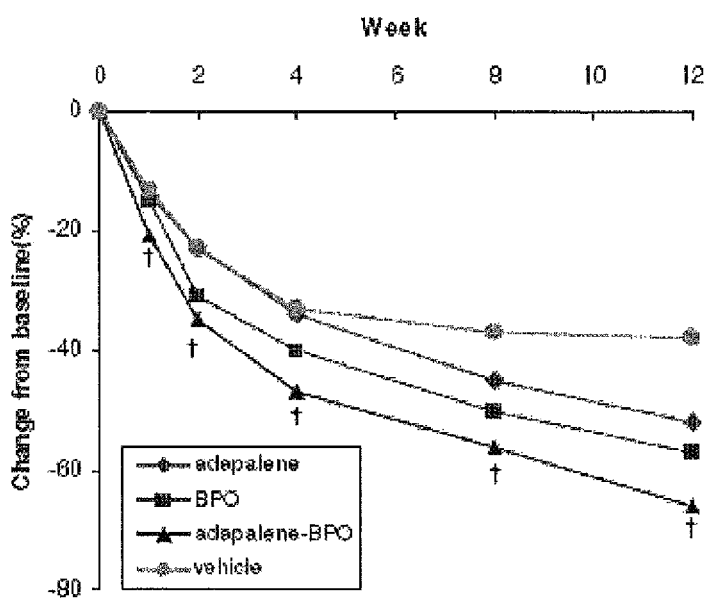
Figure 8A
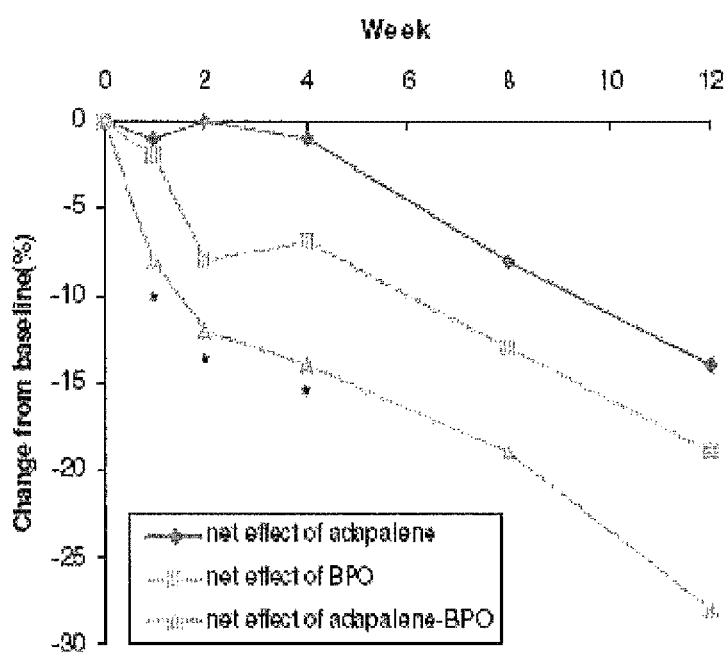
Figure 8B
| week | 1 | 2 | 4 |
|---|---|---|---|
| contribution of synergy to efficacy of adapalene-BPO | 62.5% | 33.3% | 42.9% |
Figure 8C

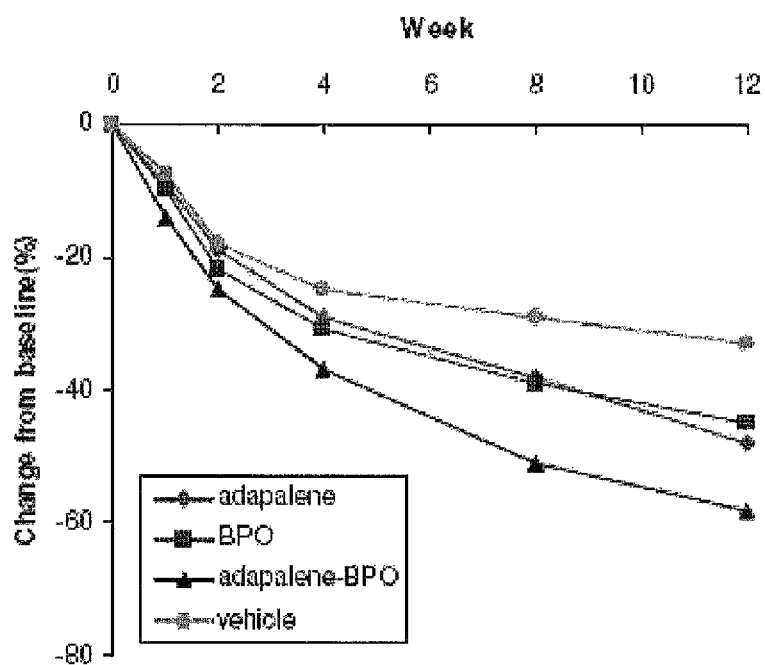
Figure 9A
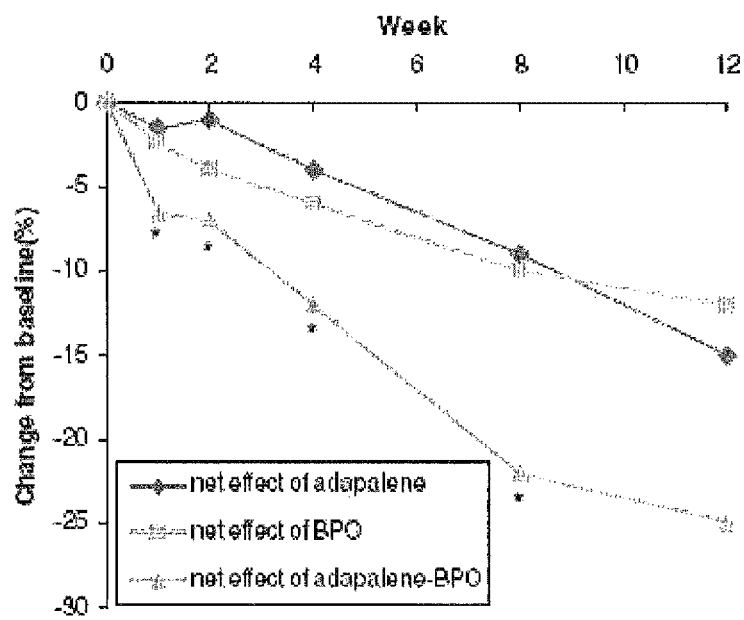
Figure 9B
| week | 1 | 2 | 4 | 8 |
|---|---|---|---|---|
| contribution of synergy to efficacy of adapalene-BPO | 40.9% | 28.6% | 16.7% | 13.6% |
Figure 9C

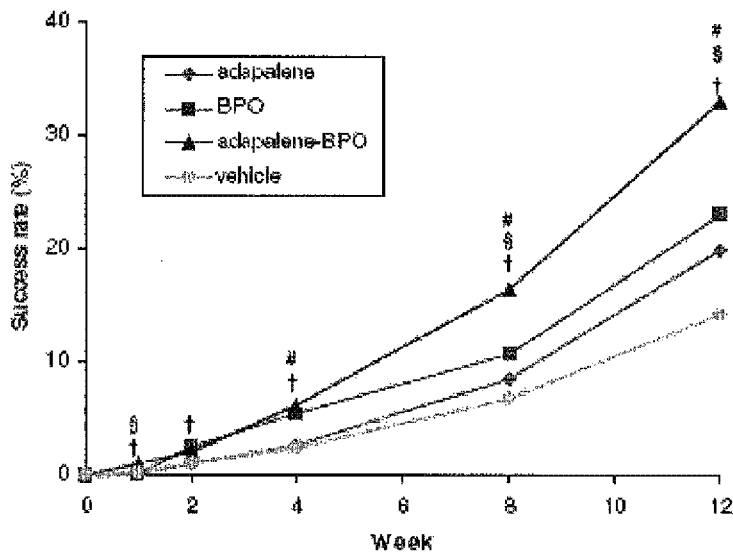
Figure 10A
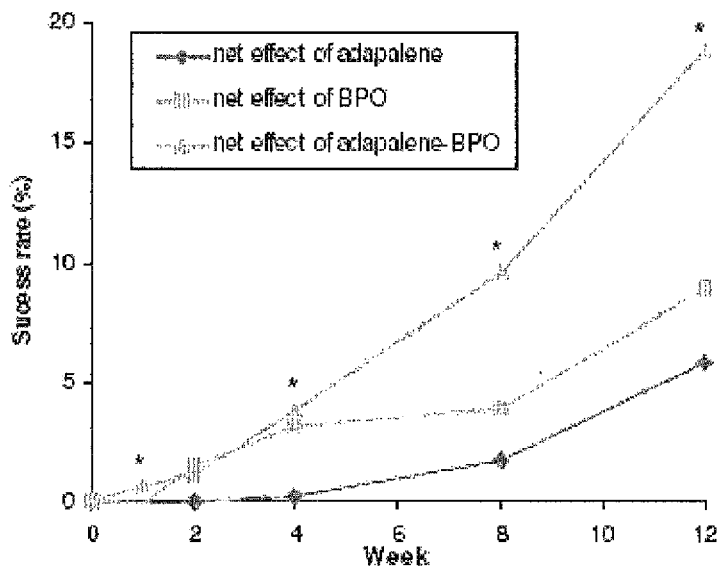
Figure 10B
| week | 1 | 4 | 8 | 12 |
|---|---|---|---|---|
| contribution of synergy to efficacy of adapalene-BPO | 128.6% | 13.2% | 41.7% | 22.2% |
Figure 10C

COMBINATIONS OF ADAPALENE AND BENZOYL PEROXIDE FOR TREATING ACNE LESIONS

CROSS-REFERENCE TO EARLIER APPLICATIONS

This application is a continuation of earlier U.S. patent application Ser. No. 12/473,981, filed May 28, 2009, now U.S. Pat. No. 8,080,537, now allowed, which is a continuation-in-part of U.S. patent application Ser. No. 12/318,937, filed Jan. 13, 2009, now U.S. Pat. No. 8,071,644, now allowed, which is a continuation of PCT/EP 2007/057207, filed Jul. 12, 2007 and designating the United States (published in the English language on Jan. 17, 2008 as WO 2008/006888 A1), which claims benefit of U.S. Provisional Application No. 60/833,491, filed Jul. 27, 2006, and also claims priority of Application No. 06/52968, filed in France on Jul. 13, 2006, each earlier application hereby expressly incorporated by reference in its entirety and each assigned to the assignee hereof.

CROSS-REFERENCE TO RELATED APPLICATIONS

This application is also related to copending U.S. application Ser. No. 13/296,186, filed Nov. 14, 2011, which is a continuation of the aforementioned U.S. application Ser. No. 12/318,937, filed Jan. 13, 2009, now allowed; and is also related to copending U.S. application Ser. No. 11/826,364, filed Jul. 13, 2007, now allowed.

BACKGROUND OF THE INVENTION

1. Technical Field of the Invention

The present invention relates to the combined or associated administration of adapalene and of benzoyl peroxide for reducing the number of acne lesions. 6-[3-(1-Adamantyl)-4-methoxyphenyl]-2-naphthoic acid (referred to hereinbelow as adapalene) is a naphthoic acid derivative with retinoid and anti-inflammatory properties. This molecule was developed for the topical treatment of common acne and of dermatoses sensitive to retinoids.

2. Description of Background and/or Related and/or Prior Art

Adapalene is marketed under the trademark Differin® at a weight concentration of 0.1%, in the form of an "alcoholic lotion" solution, an aqueous gel and a cream. These compositions are useful for treating acne. FR 2,837,101 describes adapalene compositions at a weight concentration of 0.3%, for treating acne.

WO 03/0555 472 and corresponding US 2003/0170196 moreover describe stable pharmaceutical compositions comprising adapalene and benzoyl peroxide (BPO).

An article by Korkut and Piskin, *J. Dermatology*, 2005, 32: 169-173, reports the results of a study comparing a treatment combining application of adapalene in the evening and application of BPO in the morning, relative to an application of each of the active principles alone. The authors do not observe any superiority of the combined treatment over a period of 11 weeks of treatment.

SUMMARY OF THE INVENTION

It has now been demonstrated, surprisingly, that a therapeutic association or combination of adapalene and BPO can provide a degree of success in reducing the number of acne lesions and an improvement in the clinical condition of patients that are markedly superior to those of a treatment based on adapalene alone or on BPO alone, while at the same time maintaining the same skin tolerance.

The recommended treatment may take the form of a pharmaceutical composition combining adapalene and BPO, or a concomitant application of two pharmaceutical compositions, one comprising adapalene and the other comprising BPO.

The present invention thus features formulation of adapalene or a pharmaceutically acceptable salt thereof into a pharmaceutical composition, especially at set doses, intended to be administered in combination or in association with benzoyl peroxide (BPO), for the treatment of acne lesions, especially to reduce the number of acne lesions and to improve the clinical condition of patients.

Preferably, the acne lesions are of inflammatory and/or non-inflammatory type.

Acne is initially characterized by keratinization disorders, which are sometimes invisible to the naked eye. Visible acne lesions then develop, while the size of the sebaceous glands and the production of sebum increase.

The present invention specifically concerns acne lesions. The term "acne lesions" means non-inflammatory lesions (open and closed comedones) and inflammatory lesions (papules, pustules, nodules and cysts) caused by acne. Preferably, the inflammatory lesions are treated with the association or the combination according to the invention.

More preferably, the pharmaceutical composition is administered by daily cutaneous topical application. In other words, the invention relates to the administration of adapalene as an agent for potentiating the action of BPO. Reciprocally, BPO potentiates the action of adapalene.

The term "adapalene salts" means the salts formed with a pharmaceutically acceptable base, especially mineral bases such as sodium hydroxide, potassium hydroxide and ammonia or organic bases such as lysine, arginine or N-methylglucamine. The term "adapalene salts" also means the salts formed with fatty amines such as dioctylamine and stearylamine.

The expression "combination of adapalene or salts thereof with benzoyl peroxide" means a single composition comprising both adapalene or salts thereof and benzoyl peroxide.

BRIEF DESCRIPTION OF THE DRAWINGS

FIG. 7A is a graph of the median percentage change from baseline in total lesion counts for the effect of treatments, †$P<0.05$ vs. adapalene, BPO and vehicle for the 3855 patient clinical trials;

FIG. 7B is a graph of the median percentage change from baseline in total lesion counts for the net effect of treatment (active minus vehicle), *adapalene and BPO acted synergistically, i.e., net effect of adapalene-BPO greater than the sum of net effects of adapalene alone and BPO alone, for the 3855 patient clinical trials;

FIG. 7C is a chart showing the contribution of synergy to efficacy of adapalene-BPO in the total lesion counts (synergy divided by net effect of adapalene-BPO) at selected time points over the course of the 3855 patient clinical trials;

FIG. 8A is a graph of the median percentage change from baseline in inflammatory lesion counts for the effect of treatments, †$P<0.05$ vs. adapalene, BPO and vehicle for the 3855 patient clinical trials;

FIG. 8B is a graph of the median percentage change from baseline in inflammatory lesion counts for the net effect of treatment (active minus vehicle), *adapalene and BPO acted synergistically, i.e., net effect of adapalene-BPO greater than the sum of net effects of adapalene alone and BPO alone, for the 3855 patient clinical trials;

FIG. 8C is a chart showing the contribution of synergy to the net effect of adapalene-BPO in inflammatory lesion counts (synergy divided by net effect of adapalene-BPO) at selected time points over the course of the 3855 patient clinical trials;

FIG. 9A is a graph of the median percentage change from baseline in non-inflammatory lesion counts for the effect of treatments, $P<0.05$ vs. adapalene, BPO and vehicle for the 3855 patient clinical trials;

FIG. 9B is a graph of the median percentage change from baseline in non-inflammatory lesion counts for the net effect of treatment (active minus vehicle), *adapalene and BPO acted synergistically, i.e. net effect of adapalene-BPO greater than the sum of net effects of adapalene alone and BPO alone, for the 3855 patient clinical trials;

FIG. 9C is a chart showing the contribution of synergy to the efficacy of adapalene-BPO in non-inflammatory lesion counts (synergy divided by net effect of adapalene-BPO) at selected time points over the course of the 3855 patient clinical trials;

FIG. 10A is a graph of the success rate for the effect of treatments in the 3855 patient clinical trials, †$P<0.05$ vs. adapalene, §$P<0.05$ vs. BPO; #$P<0.05$ vs. vehicle;

FIG. 10B is a graph of the net effect of treatments (active minus vehicle) for the 3855 patient clinical trials, *adapalene and BPO acted synergistically, i.e., net effect of adapalene-BPO greater than the sum of net effects of adapalene alone and BPO alone;

FIG. 10C is a chart showing the contribution of synergy to efficacy of adapalene-BPO (synergy divided by net effect of adapalene-BPO) at selected time points over the course of the 3855 patient clinical trials;

Figure 1:
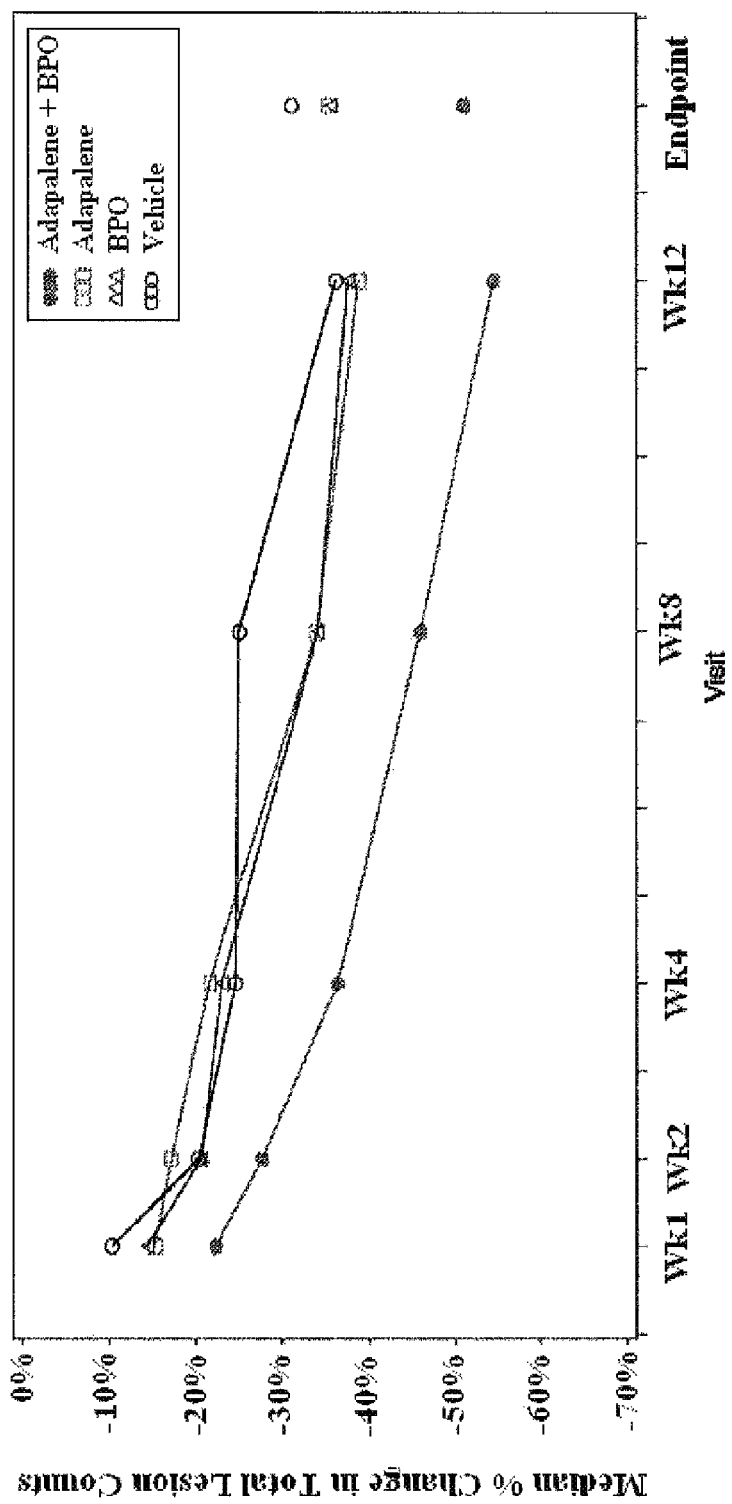
FIGS. 1-3 are graphs showing the change in the number of lesions over time, upon treatment either according to the invention or not.

DETAILED DESCRIPTION OF BEST MODE AND SPECIFIC/PREFERRED EMBODIMENTS OF THE INVENTION

According to one preferred embodiment, the pharmaceutical composition is a fixed combination and comprises, in a pharmaceutically acceptable medium, (i) at least one compound selected from among adapalene and pharmaceutically acceptable salts thereof, and (ii) benzoyl peroxide (BPO). Preferably, the pharmaceutical composition is intended for a single topical application per day.

The term "pharmaceutically acceptable medium" means a medium that is compatible with the skin, mucous membranes and the integuments.

The term "fixed combination" should be understood as meaning a combination whose active principles are combined at fixed doses in the same vehicle (single formula) that delivers them together to the point of application. Preferably, the pharmaceutical composition in the form of a fixed combination is a gel; in this case, the two active principles are dispersed and intimately mixed, during production, in the same vehicle, which delivers them together during the application of the gel.

In another embodiment of the invention, the pharmaceutical composition is in the form of a composition A comprising adapalene, suited to be applied concomitantly with a composition B comprising BPO. Preferably, composition A and composition B are presented in the form of a kit, preferably comprising two isolated compartments each containing one of the two pharmaceutical compositions A or B (dual pack) and allowing simultaneous administration of the two compositions, or alternatively in the form of a kit combining in the same presentation at least the two products (compositions A and B) in two separate packages, preferably in the form of tubes (co-packaging).

In this case, one skilled in this art will adapt the formula that is the most appropriate in terms of viscosity, additives, etc. to the selected kit.

The expression "concomitant" application means that the compositions are suited to be applied to the skin simultaneously or one after the other, in any order, or in a sequential order (for example, in which the application of a pharmaceutical composition B comprising BPO precedes the application of the pharmaceutical composition A comprising adapalene), but within a time interval of less than 1 hour, preferably less than 30 minutes, preferably less than 15 minutes, more preferably less than 5 minutes or even less than 1 minute.

The present invention thus also features compositions in kit form comprising at least two components:

a first component comprising at least adapalene or a pharmaceutically acceptable salt thereof, a second component comprising benzoyl peroxide, these two components being suited to be applied concomitantly to the skin, mucous membranes and/or the integuments.

Compositions A and B are preferably useful for a single cutaneous topical application per day.

The treatments have a variable duration, depending on the patient and the severity of his acne. The treatment period may thus run from several weeks to several months. A suitable treatment period is at least two weeks, preferably from 1 to 6 months and more preferably a duration of about 3 months is preferable, the duration of the treatment possibly being prolonged, if necessary.

All the pharmaceutical compositions of the invention may comprise from 0.01% to 2%, preferably from 0.05% to 0.5% and preferentially from 0.1% to 0.3% of adapalene, and from 0.1% to 20% and preferably from 0.5% to 10% of BPO, more preferably from 2% to 5% of BPO and preferentially 2.5% of BPO.

All the percentages are indicated by weight relative to the total weight of the composition.

The adapalene:BPO ratio ranges from 1:1 to 1:200 and, conversely, the BPO:adapalene ratio ranges from 1:1 to 1:200. Preferably, the adapalene:BPO ratio ranges from 1:1 to 1:200 and the adapalene:BPO ratio is preferably 1:25.

Preferably, the effect of the combination of the two active principles is at least an additive effect and preferentially a potentiation or synergistic effect. The terms "potentiation effect" and "synergistic effect" mean a therapeutic effect (degree of success) greater than the effect resulting from the addition of the effects obtained by each of the two active principles taken separately.

When they are combined in the same pharmaceutical composition, the adapalene and the BPO are present in the pharmaceutical composition in synergistic amounts, i.e., such that a synergistic or potentiation effect on the acne lesions and on the clinical condition of the patient is observed. Preferably, the pharmaceutical composition comprises 0.1% of adapalene and 2.5% of BPO.

When compositions A and B are administered separately, the adapalene and the BPO are, respectively, present in composition A and composition B in synergistic amounts, i.e., such that a synergistic or potentiation effect on the acne lesions and on the clinical condition of the patient is observed, especially when the compositions are applied in association in equal amounts. Preferably, composition A comprises 0.1% of adapalene and composition B comprises 2.5% of BPO.

In this regard, the examples to follow demonstrate that because of the synergistic effect of adapalene and BPO, the invention provides greater efficacy for the treatment of acne in general and of acne lesions in particular and a quicker onset of action relative to monotherapies.

The pharmaceutical compositions according to the invention may be in the form of ointments, emulsions preferably in the form of creams, milks or pomades; powders, impregnated pads, solutions, gels, sprays, lotions or suspensions. They may also be in the form of suspensions of microspheres or nanospheres or of lipid or polymer vesicles or of polymer patches and/or of hydrogels allowing controlled release. These compositions may be in anhydrous form, in aqueous form or in the form of an emulsion.

In one preferred embodiment of the invention, the pharmaceutical compositions are in the form of a gel, a cream or a solution referred to as a lotion.

Preferably, the pharmaceutical compositions combining adapalene and BPO, or the pharmaceutical compositions A and/or B, are gels.

The pharmaceutical compositions of the invention may contain inert additives or combinations of these additives, such as:
  wetting agents;
  texture enhancers;
  preservatives such as para-hydroxybenzoic acid esters;
  stabilizers;
  humidity regulators;
  pH regulators;
  osmotic pressure modifiers;
  emulsifiers;
  UV-A and UV-B screening agents; and
  antioxidants, such as α-tocopherol, butylhydroxyanisole or butylhydroxytoluene, superoxide dismutase, ubiquinol, or certain metal-chelating agents.

Needless to say, one skilled in this art will take care to select the optional compound(s) to be added to these compositions such that the advantageous properties intrinsically associated with the present invention are not, or are not substantially, adversely affected by the envisaged addition.

According to one particular embodiment, the pharmaceutical composition A comprising adapalene may be an aqueous gel especially containing one or more ingredients selected from among the carbomer 940 (BF Goodrich Carbopol 980) and propylene glycol, or a cream especially containing one or more ingredients selected from among perhydrosqualene, cyclomethicone, PEG-20 methylglucose sesquistearate and methylglucose sesquistearate or an "alcoholic lotion" solution based on polyethylene glycol.

Useful pharmaceutical compositions, comprising adapalene and BPO, are moreover described in WO 03/055 472. Examples of such compositions comprise, besides the active principles adapalene and BPO:
  from 5% to 25% of water;
  from 0 to 10%, preferably from 0 to 2% and preferably less than 0.5% of liquid wetting surfactant;
  from 0 to 10% of pro-penetrating agent; and
  an aqueous phase comprising a pH-independent gelling agent.

According to one preferred embodiment, the preferred pharmaceutical composition, comprising adapalene and BPO, is an aqueous gel having the following formulation:
  2.5% of BPO;
  0.1% of adapalene;
  0.10% of disodium EDTA;
  4.00% of glycerol;
  4.00% of propylene glycol;
and also, preferably:
  0.05% of sodium;
  0.20% of poloxamer 124;
  4.00% of sodium acryloyldimethyltaurate copolymer and isohexadecane and polysorbate 80;
  NaOH, in an amount sufficient to obtain a pH of 5.

The acne targeted comprises all forms of acne, including common acne, comedones, polymorphs, nodulocystic acne, acne conglobata, and secondary acne such as solar, medicational or occupational acne. The acne may in particular be of mild to severe intensity and preferably of mild to moderate intensity. The compositions according to the invention may be administered as a firstline treatment, and also after failure of other specific treatments including the administration of adapalene and/or of BPO according to the conditions described by Korkut et al.

The association or combination of adapalene and of BPO makes it possible to reduce not only the number of inflammatory acne lesions but also the non-inflammatory acne lesions and to observe an improvement in the patient's clinical condition. A potentiation or synergistic effect is observed. This potentiation effect described in the example to follow is shown in the reduced number of lesions and in the percentage of cured patients (clear) and almost cured patients (almost clear) by the size of the superiority of the combination at fixed doses of adapalene and of BPO, relative to the active substances taken individually at the same doses as the combination.

Moreover, the results of the potentiation effect of the combination of adapalene and BPO presented in the example are statistically different from the results obtained for the active substances taken individually.

The combination or association of adapalene and of BPO is thus particularly useful for reducing the number of inflammatory and/or non-inflammatory acne lesions. Preferably, the reduction is at least about 40%, preferably at least about 50% and more preferably the reduction is at least about 60%. Similarly, it is demonstrated in the example that the reduction of the total lesions is from about 35% to 80% and preferably from about 50% to 70%.

According to another embodiment, this invention also features a pharmaceutical assembly (product) comprising:

i) a container delimiting at least one compartment, the said container being closed by means of a closing member; and ii) a pharmaceutical composition comprising adapalene or a pharmaceutically acceptable salt thereof and benzoyl peroxide as described above, and placed inside the said compartment.

The container may be in any suitable form. It may especially be in the form of a bottle, a tube, a jar, a case, a can, a sachet or a box.

Preferably, the container comprises two compartments, and each of these compartments comprises either composition A or composition B.

The closing member may be in the form of a removable stopper, a lid, a cover, a tear-off strip or a cap, especially of the type comprising a body fixed to the container and a cap articulated on the body. It may also be in the form of a member ensuring the selective closure of the container, especially a pump, a valve or a clapper.

The closing member may be coupled to the container by screwing. Alternatively, the coupling from the closing member and the container may take place other than by screwing, especially via a bayonet mechanism, by click-fastening, gripping, welding, bonding or magnetic attraction. The term "click-fastening" in particular means any system involving the passing of a rim or bead of material by elastic deformation of a portion, especially of the closing member, followed by return to the elastically unstressed position of the said portion after the rim or bead has been passed.

The container may be at least partly made of thermoplastic material. Examples of thermoplastic materials include polypropylene and polyethylene.

Alternatively, the container is made of a non-thermoplastic material, especially of glass or metal (or alloy).

The container may have rigid walls or deformable walls, especially in the form of a tube or a tube bottle.

The container may comprise means for causing or facilitating the distribution of the composition. By way of example, the container may have deformable walls so as to make the composition come out in response to a positive pressure inside the container, this positive pressure being caused by elastic (or non-elastic) squeezing of the walls of the container. Alternatively, especially when the product is in the form of a stick, this stick may be driven by a piston mechanism. Still in the case of a stick, especially of makeup product, the container may comprise a mechanism, especially a wishbone mechanism, or a mechanism with a threaded stem, or with a helical ramp, which is capable of moving a stick in the direction of the said opening. Such a mechanism is described, for example, in FR 2,806,273 or in FR 2,775,566. Such a mechanism for a liquid product is described in FR 2,727,609.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Example 1

Clinical Study Results

A clinical study for confirmation of efficacy was performed for a topical gel combining adapalene+benzoyl peroxide (BPO).

This gel has the following formulation (expressed as % weight/total weight):

| | |
|---|---|
| Adapalene | 0.10% |
| Benzoyl peroxide | 2.50% |
| Copolymer of acrylamide & sodium acryloyldimethyltaurate | 4.00% |
| Sodium docusate | 0.05% |
| Disodium EDTA | 0.10% |
| Glycerol | 4.00% |
| Poloxamer 124 | 0.20% |
| Propylene glycol | 4.00% |
| Purified water | qs 100% |

Protocol:

The clinical study was a multi-center, randomized, double-blind study in parallel groups, to evaluate the tolerance and the efficacy of the above formulation, in comparison with its own individual active substances placed at the same doses in gels of the same formula as that of the fixed combination (individual formulae referred to as "monads") and in comparison with the gel vehicle (placebo formula): adapalene gel (0.1%), BPO gel (2.5%) and vehicle gel.

All the treatments were applied once a day for 12 weeks, to 517 patients suffering from acne.

The main efficacy criteria were:

the degree of success, defined as the percentage of patients considered as being "clear", i.e., the patient has no more acne lesions (neither comedones nor inflammatory lesions), reflecting an improvement in the patient's clinical condition, or "almost clear" on the evaluation scale;

the reduction of the percentage of inflammatory and non-inflammatory lesions after 12 weeks of treatment.

Results:

The results are presented in the Table that follows.

Figure 2:
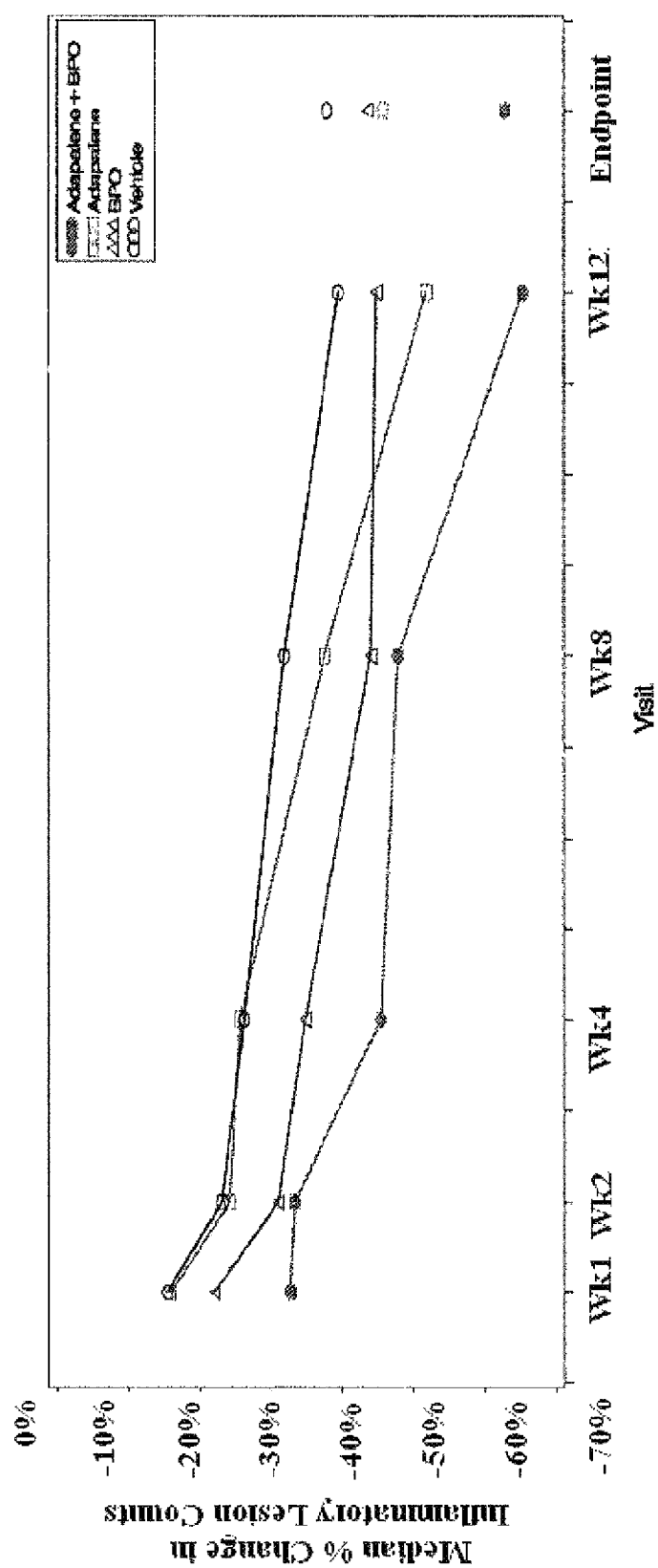
Figure 3:
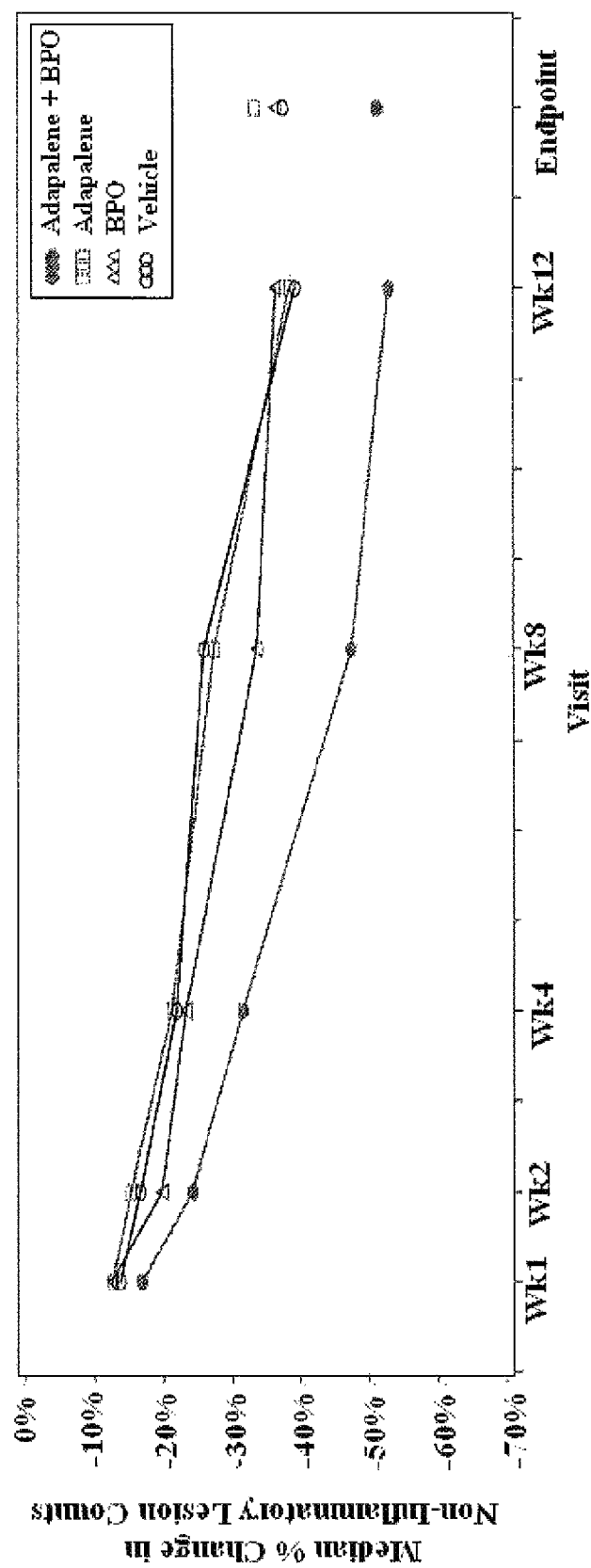
Figure 4:
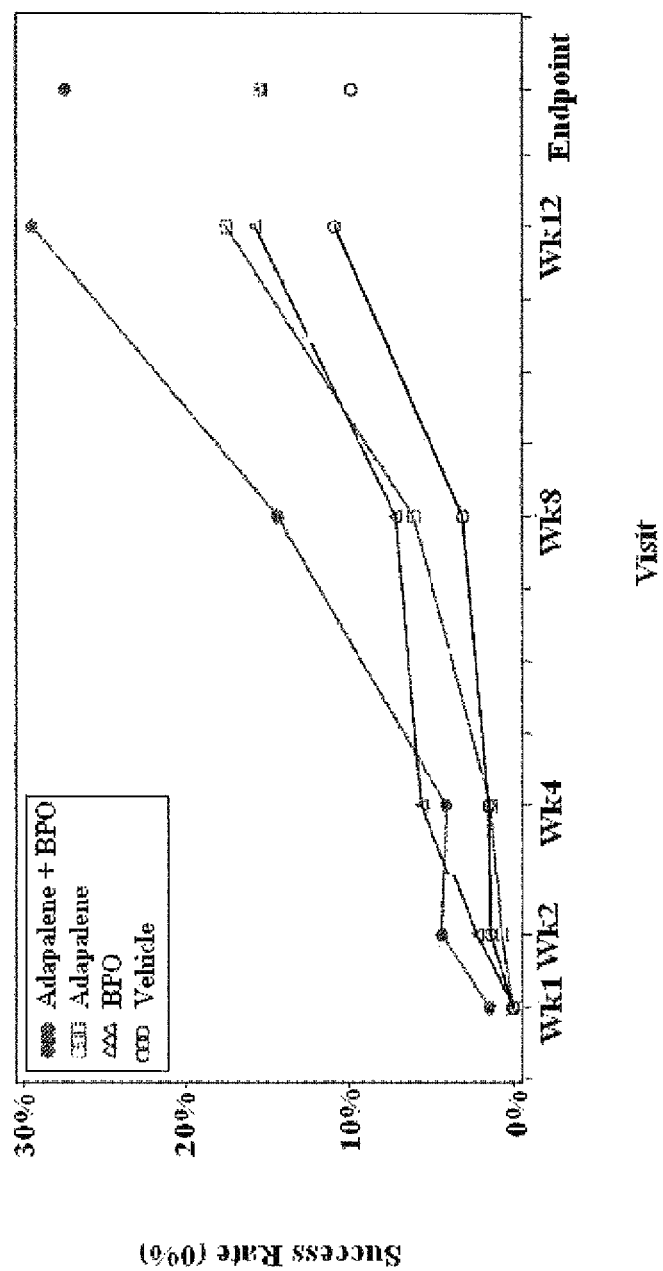
FIG. 4 is a graph showing the degree of success over time of treatment according to the invention or not.

| | Efficacy in week 12 ITT* | | | |
|---|---|---|---|---|
| | Adapalene 0.1% + BPO 2.5% N = 149 | Adapalene 0.1% alone N = 148 | BPO 2.5% alone N = 149 | Vehicle (gel) N = 71 |
| Degree of success (see FIG. 4) | 27.5% | 15.5% | 15.4% | 9.9% |
| Progress of the lesions (median percentages) | | | | |
| Number of inflammatory lesions (see FIG. 2) | −62.8% | −45.7% | −43.6% | −37.8% |
| Number of non-inflammatory lesions (see FIG. 3) | −51.2% | −33.3% | −36.4% | −37.5% |
| Total number of lesions (see FIG. 1) | −51.0% | −35.4% | −35.6% | −31.0% |
| Progress of the lesions (as median absolute numbers) | | | | |
| Number of inflammatory lesions | −17 | −13.0 | −13.0 | −11.0 |
| Number of non-inflammatory lesions | −22.0 | −17.0 | −16.0 | −14.0 |
| Total number of lesions | −40.0 | −29.0 | −27 | −26.0 |

ITT* (analysis of intention to treat): all the patients randomized in a clinical test because they come under the indication selected for the treatment to be prescribed.
The missing data are imputed by the last observation (LOCF method ** (Last Observation Carried Forward).

1) For the 4 main criteria of the study: degree of success and progress as a percentage of the three types of lesion, the fixed combination was found to be statistically superior to the two monads and to the vehicle.

2) When the effect of the gel used as vehicle (V) is subtracted from the effect of the fixed combination (C), the net clinical benefit of the fixed combination (C−V) is numerically superior to the sum of the net clinical benefits of each of the individual substances after subtraction of the vehicle effect from the adapalene (A) and BPO (B) branches, respectively, according to the equation:

$$(C-V) > (A-V) + (B-V).$$

These results systematically show a potentiation effect since the net benefit is in favor of the gel combining adapalene+BPO, with results, in terms of degree of success, that are superior to the addition of adapalene and BPO (28% for the combination, as opposed to 16%, 15% to 10% for adapalene, BPO and vehicle, respectively). In this case, the above equation shows (28−10)>(16−10)+(15−10), i.e., 18>11, which is true.

Similarly, the gel combining adapalene+BPO was numerically superior in terms of efficacy in comparison with the individual active substances and with the vehicle as regards the reduction in the number of all the lesions (reduction in the percentage of inflammatory and non-inflammatory lesions).

A potentiation effect of adapalene and BPO together is thus noted, since a 51% reduction in lesions is observed for the combination, as opposed to 35% for adapalene alone, 36% for BPO alone and 31% for the vehicle, which is expressed as a net benefit of efficacy with the above equation by (51−31)>(35−31)+(36−31), i.e., 20>9, which is true.

Example 2

Evaluation of the Anti-Inflammatory in Ear Oedema Model on Balb/c Mice

The study was carried out with 45 (5 par groups) female 9 weeks aged Balb/c ByJlc mice.

The Edema was induced by a single application of 20 μl of TPA dissolved in acetone at 0.01%.

The treatment was administrated by single topical application of tested compounds dissolved in TPA at 0.01% (groups 3, 4, 5, 6 and 7) and dissolved in TPA 0.01%+BPO (groups 8, 9 and 10).

The treatments activity was measured by inflammation evaluation with ear thickness at T+6 hours.

Figure 5:
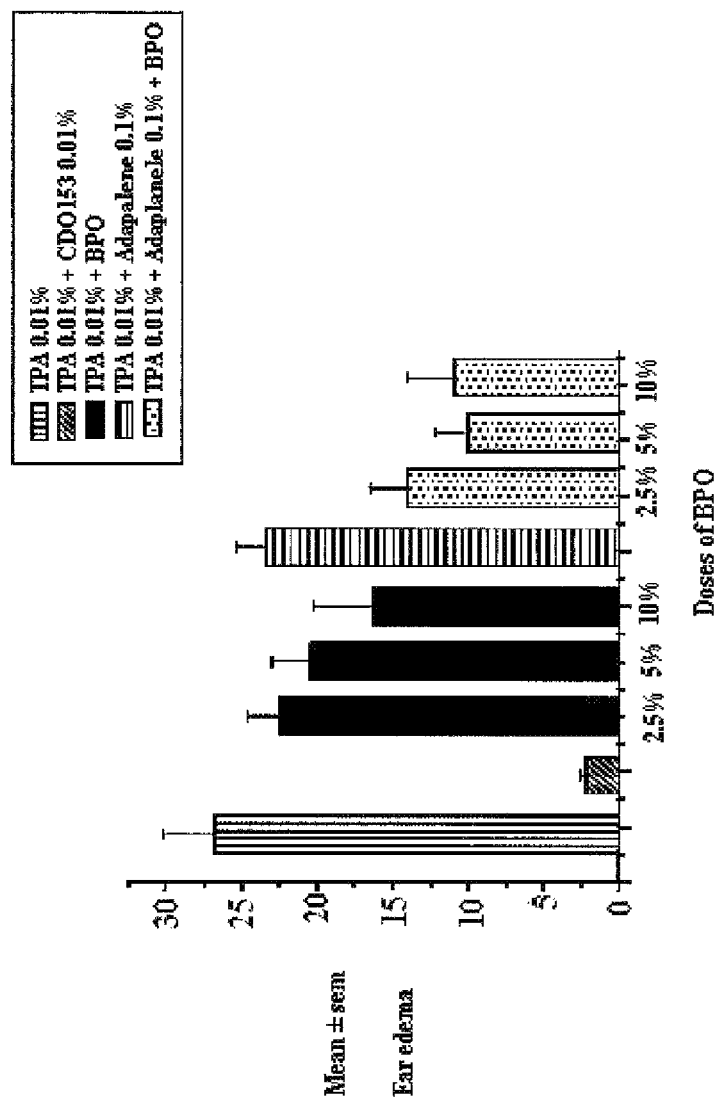
FIG. 5 is a bar graph evaluating the anti-inflammatory effect on ear edema of treatment according to the invention or not.

The results are presented in the following table and in FIG. 5.

Conclusion:

After a single topical application of the positive control CD0153 (0.01%) diluted in TPA solution, we observed a decrease of 92% of the ear thickness.

BPO at 2.5%, 5% and 10% has a slight anti-inflammatory effect, reducing the TPA-induced ear edema respectively by 16%, 24% and 40%, with a statistically significant dose balanced effect (0.042).

Adapalene alone has a low anti-inflammatory effect, reducing the TPA-induced ear edema by 13%.

Variation of concentration of BPO was measured in combination with adapalene. Therefore, combinations of BPO at 2.5%, 5% and 10% with Adapalene at 0.1% reduce the TPA-induced ear edema respectively by 48%, 63% and 59%. Combination treatment is statistically more efficient than BPO alone (0.0015) even though the dose effect of the latest group is non-significant regarding the TPA alone group (0.1089).

Adapalene at 0.1% increases the anti-inflammatory effect obtained with BPO whatever the tested doses.

Lower doses of BPO will be used to attempt to show a dose related effect for the association.

These results show a potential synergistic anti-inflammatory effect of the combination compared to the compounds singly applied.

Further Clinical Testing

The results of several clinical trials (total of 3855 acne vulgaris patients) were analyzed to determine whether adapalene and benzoyl peroxide (BPO) demonstrate a synergistic efficacy in the fixed dose combination of 0.1% adapalene and 2.5% benzoyl peroxide.

Introduction

Combination therapy is frequently employed for management of acne vulgaris due to the multi-factorial pathogenesis of the disease.[1-4] Acne development involves multiple pathophysiologic factors, including increase of sebum production, ductal hypercornification, P. acnes proliferation and inflammation/immunological response.[5] Topical monotherapies such as retinoids, antibiotics and benzoyl peroxide (BPO) target one or two of those factors; whereas combination therapy utilizing agents with complementary mode of action provides possibility of targeting multiple factors simultaneously. Combination therapy with topical retinoids and antimicrobial agents is faster and more efficacious than antimicrobial therapy alone in reducing both inflammatory and non-inflammatory lesions,[6-9] and is therefore recommended in an international consensus guideline.[5]

A fixed-dose topical combination gel containing adapalene 0.1% and BPO 2.5% has recently been developed for once-daily treatment of acne. The distinct mechanisms of action

|  | Ear edema | | Inhibition | Repeated Annova Testing vs TPA alone | Repeated Annova Testing vs TPA + BPO |
| --- | --- | --- | --- | --- | --- |
| Acetone | Mean | sem | vs TPA (%) | (Dose balanced) | (Dose balanced) |
| TPA 0.01% | 26.80 | 3.35 | | | |
| TPA 0.01 + CD153 0.01% (controle) | 2.20 | 0.37 | 91.8 | 0.042 | |
| TPA 0.01% + BPO at 2.5% | 22.40 | 2.23 | 16.4 | | |
| TPA 0.01% + BPO at 5% | 20.40 | 2.62 | 23.9 | | |
| TPA 0.01% + BPO at 10% | 16.20 | 4.03 | 39.6 | | |
| TPA 0.01% + Adapalene at 0.1% | 23.40 | 2.01 | 12.7 | | 0.0015 |
| TPA 0.01% + Adapalene at 0.1% + BPO at 2.5% | 14.00 | 2.51 | 47.8 | | |
| TPA 0.01% + Adapalene at 0.1% + BPO at 5% | 10.00 | 2.26 | 62.7 | | |
| TPA 0.01% + Adapalene at 0.1% + BPO at 10% | 11.00 | 3.03 | 59.0 | | | and good efficacy/safety profiles of adapalene and BPO make them a logical choice for combination agents. Adapalene is as efficacious as other retinoids but has a much lower irritation potential.[10] It possesses anticomedogenic, comedolytic and anti-inflammatory properties, and can be also used for long-term maintenance.[10] BPO is the most potent bactericidal agent among all topical antibiotics,[11] and has the additional advantage of not being associated with selective pressure of bacterial resistance.[12] In addition, adapalene remains stable when combined with BPO even in the presence of light.[13] Furthermore, it has been demonstrated that adapalene can be used in conjunction with other therapies without notably increasing the incidence of skin irritation.[14-18] Three multi-center, double-blind, randomized and controlled studies on adapalene-BPO were conducted, and the results demonstrated a favorable efficacy/safety profile of the combination gel.[19-21] Patients also reported to be more satisfied with the effectiveness and the overall treatment of adapalene-BPO than with the respective monotherapies and the gel vehicle.[20, 21]

Several combination treatments of acne utilizing antibiotics and BPO or tretinoin are currently available.[22-24] The synergistic efficacy of individual components in those combinations had never been reported, although the combinations were demonstrated to be more efficacious than the corresponding monotherapies. In the present report, we perform a pooled analysis on the data of three adapalene-BPO studies involving a total of 3855 patients, and demonstrate a unique synergistic therapeutic activity of adapalene and BPO when used in the fixed-dose combination gel for treatment of acne vulgaris.

Methods and Material

Study Design

Three multicenter, double-blind, randomized and controlled studies on the efficacy and safety of adapalene-BPO were conducted in 157 centers in the U.S., Puerto Rico, Canada, Germany, Poland and Hungary.[19-21] Patients were randomized to receive adapalene 0.1%-BPO 2.5% (Epiduo®, Galderma Laboratories), adapalene 0.1%, BPO 2.5% or vehicle once daily in the evening for 12 weeks. Adapalene and BPO used in the studies were formulated in the same gel vehicle as adapalene-BPO, instead of as the respective commercial products (Differin® and Benzac®, Galderma Laboratories). Efficacy and safety assessments were performed at each study visit, occurred at baseline, weeks 1, 2, 4, 8 and 12.

These three studies were conducted in accordance with the Declaration of Helsinki, Good Clinical Practices (GCPs) and local regulatory requirements. Studies were approved by institutional review boards and ethics committees. All patients provided written informed consent prior to entering the studies.

Patient Selection

Eligible patients were 12 years or older with 20 to 50 inflammatory lesions (IL), 30 to 100 non-inflammatory lesions (NIL), no cysts and no more than 1 nodule on the face. Patients enrolled in two of the three studies (a total of 3338) had an investigator's global assessment (IGA) of 3, corresponding to "moderate" acne. Lesion counts were performed on the face only excluding the nose. Specified washout periods were required for patients taking certain topical and systemic treatments. Patients were excluded if they received systemic acne treatment or had dermatological conditions requiring interfering treatments. Women were excluded if they were pregnant, nursing, or planning a pregnancy. Men were excluded if they had facial hair that would interfere with assessments.

Efficacy and Safety Assessments

Efficacy assessments at each study visit included percentage change from baseline in lesion counts (IL, NIL and total lesion) and success rate, defined as the percentage of patients who had an IGA of "clear" or "almost clear". IGA was evaluated on a scale from 0 (clear: residual hyperpigmentation and erythema may be present) to 4 (severe: entire face is involved, covered with comedones, numerous papules and pustules, and few nodules and cysts).

Safety of the treatments was evaluated through reporting of adverse events (AE) and assessments of local facial tolerability. At each study visit, the investigators rated signs of erythema, scaling, dryness and stinging/burning on a scale from 0 (none) to 3 (severe).

Statistical Analyses

Data from the three studies were pooled and analyzed. Efficacy was evaluated in the intent-to-treat (ITT) population, which included all patients who were randomized and dispensed study medicine. Safety was assessed in the safety population, which included all patients who were randomized and treated at least once.

Efficacy was evaluated by the Cochran-Mantel-Haenzsel (CMH) test, using general association for success rate and row mean differences by relative to identified distribution (RIDIT) transformed scores for percent lesion change. All tests were 2-sided.

Definition and Calculation of Synergy

Synergy was defined as the efficacy of combination (adapalene-BPO) greater than the sum of efficacy of individual components (adapalene alone and BPO alone). We took into account the vehicle effect by deducting it from the effect of treatments:[25]

Net effect of active agent=effect of active agent−effect of vehicle Synergy=Net effect of adapalene-BPO−(Net effect of adapalene+Net effect of BPO)>0

The degree of synergy was evaluated based on the contribution of synergy to efficacy (net effect) of adapalene-BPO:

Degree of synergy (%)=(synergy/Net effect of adapalene-BPO)×100

Results

Patient Disposition and Baseline Disease Characteristics

Figure 6:
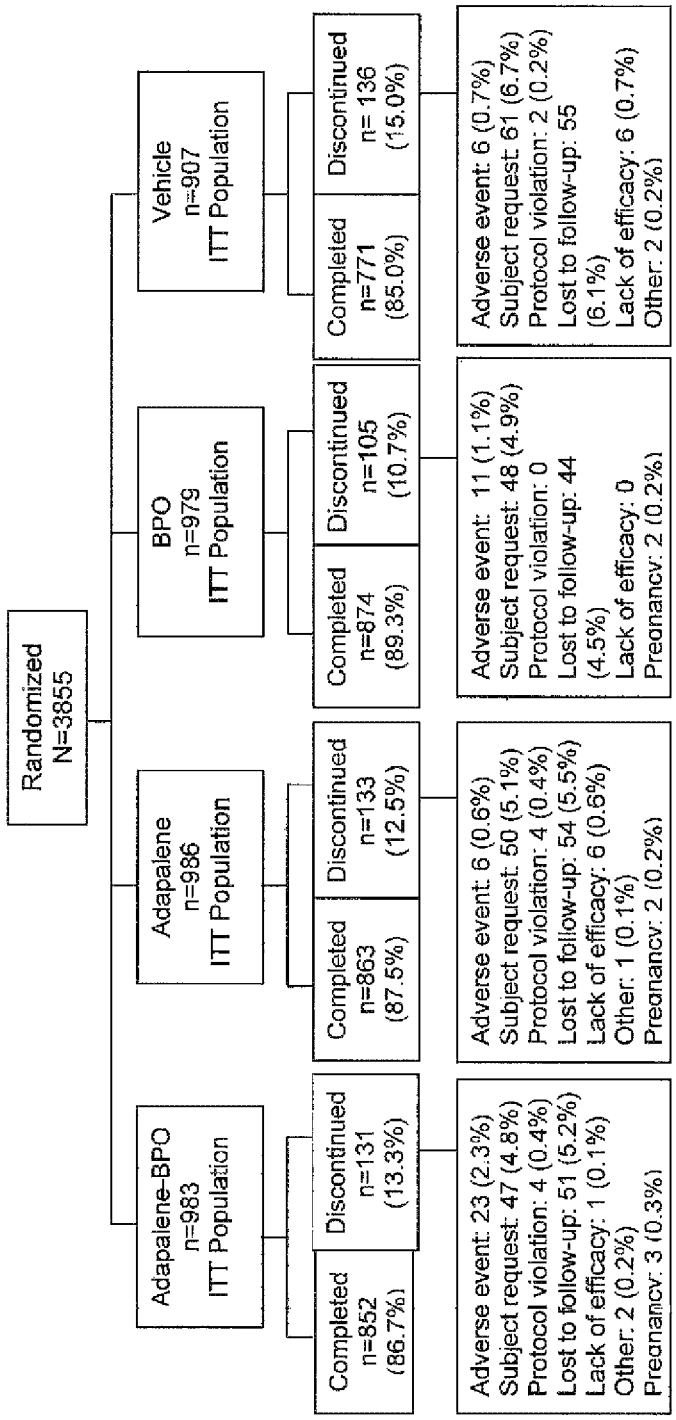
FIG. 6 is a chart showing the patient disposition and baseline disease characteristics for clinical trials of 3855 acne vulgaris patients.
Figure 11A:
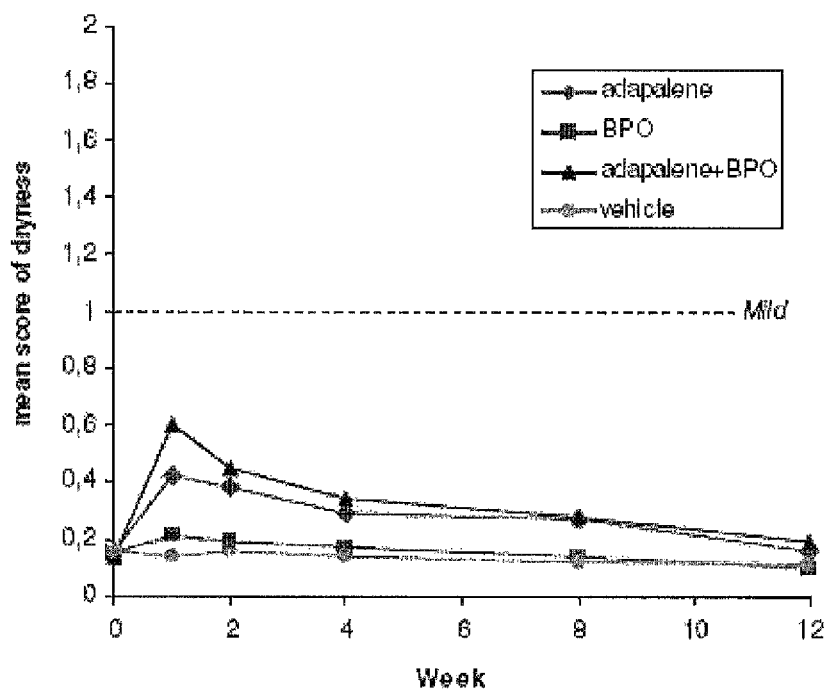
FIG. 11A is a graph of local tolerability signs showing mean scores for the severity of dryness over the course of the 3855 patient clinical trials.
Figure 11B:
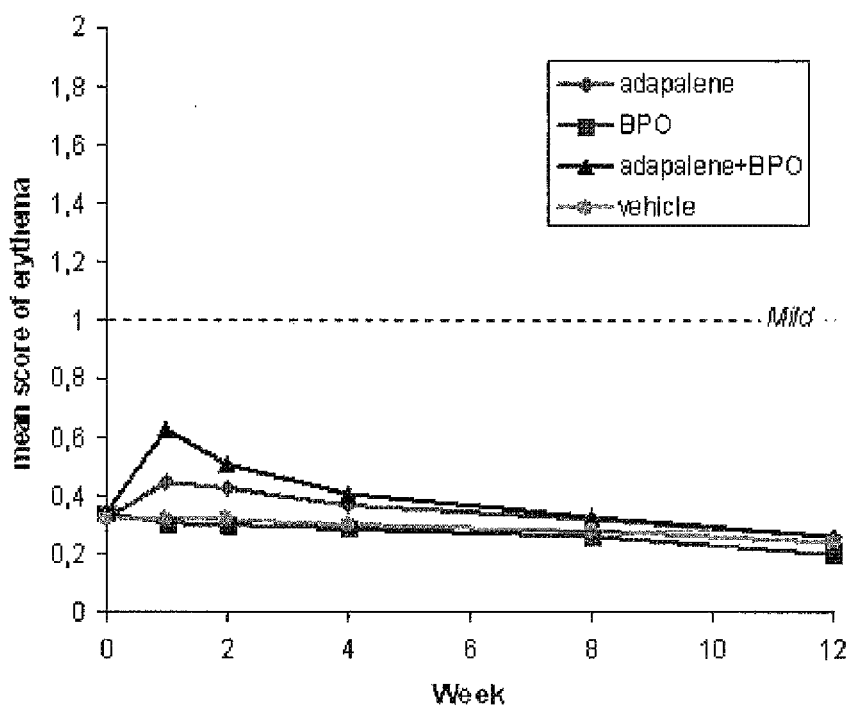
FIG. 11B is a graph of local tolerability signs showing mean scores for the severity of erythema over the course of the 3855 patient clinical trials.
Figure 11C:
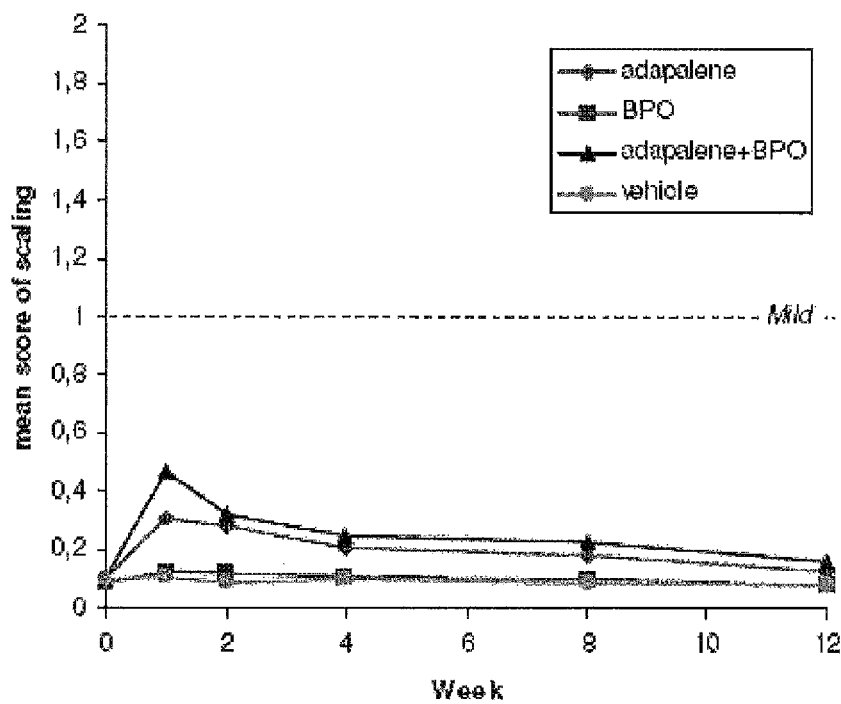
FIG. 11C is a graph of local tolerability signs showing mean scores for the severity of scaling over the course of the 3855 patient clinical trials.
Figure 11D:
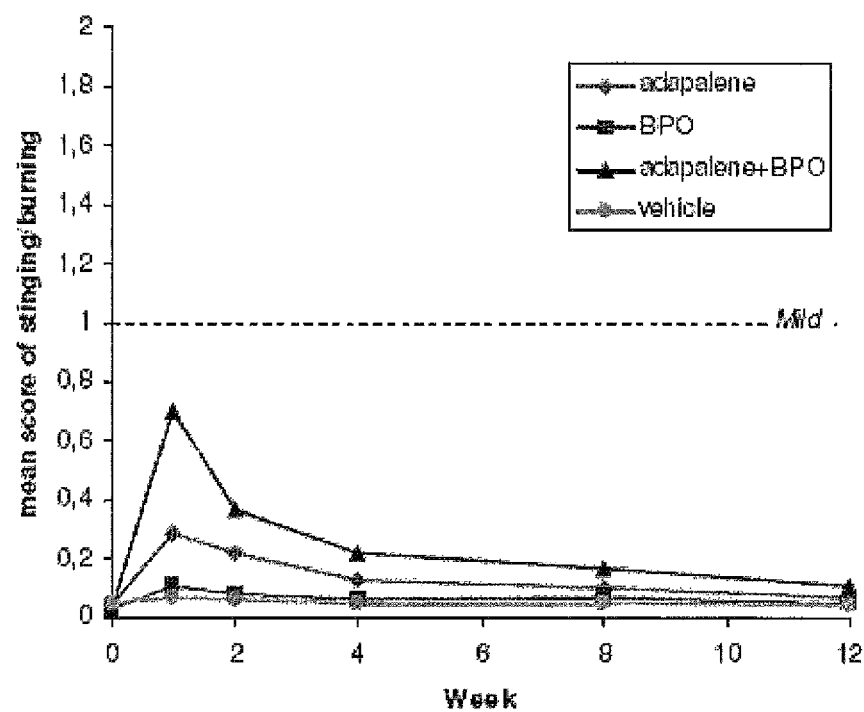
FIG. 11D is a graph of local tolerability signs showing mean scores for the severity of stinging/burning over the course of the 3855 patient clinical trials.

The ITT population included a total of 3855 patients: adapalene-BPO (n=983), adapalene (n=986), BPO (n=979) and gel vehicle (n=907) (FIG. 6). Patient disposition was similar among treatment groups. On average, 87.2% of patients completed the studies and only 1.2% discontinued due to "adverse event (AE)".

Table 1 summarizes the demographic and baseline disease characteristics, which were comparable among treatment groups. Mean age of enrolled patients was 18.3 years and the majority of patients were Caucasians (72.0%).

TABLE 1

| Demography and baseline disease characteristics. | | | | | |
|---|---|---|---|---|---|
| | Adapalene (N = 986) | BPO (N = 979) | Adapalene-BPO (N = 983) | Vehicle (N = 907) | Total (N = 3855) |
| Age, year | | | | | |
| Mean | 18.0 | 18.3 | 18.7 | 18.4 | 18.3 |
| Min, max | 12, 50 | 12, 56 | 12, 58 | 12, 51 | 12, 58 |
| Gender, N (%) | | | | | |
| Male | 478 (48.5) | 489 (49.9) | 475 (48.3) | 410 (45.2) | 1852 (48.0) |
| Female | 508 (51.5) | 490 (50.1) | 508 (51.7) | 497 (54.8) | 2003 (52.0) |
| Race, N (%) | | | | | |
| Caucasian | 712 (72.2) | 701 (71.6) | 709 (72.1) | 653 (72.0) | 2775 (72.0) |
| Black | 121 (12.3) | 130 (13.3) | 121 (12.3) | 117 (12.9) | 489 (12.7) |
| Asian | 19 (1.9) | 22 (2.2) | 20 (2.0) | 24 (2.6) | 85 (2.2) |
| Hispanic | 115 (11.7) | 105 (10.7) | 112 (11.4) | 103 (11.4) | 435 (11.3) |
| Other | 19 (1.9) | 21 (2.1) | 21 (2.1) | 10 (1.1) | 71 (1.8) |
| Median lesion counts | | | | | |
| total | 77 | 75 | 76 | 76 | 76 |
| inflammatory | 27 | 27 | 27 | 27 | 27 |
| Non-inflammatory | 46 | 45 | 44 | 46 | 45 |
| Global Severity, N (%) | | | | | |
| 2: Mild | 28 (2.8) | 15 (1.5) | 25 (2.5) | 13 (1.4) | 81 (2.1) |
| 3: Moderate | 949 (96.2) | 956 (97.7) | 953 (97.0) | 889 (98.3) | 3747 (97.2) |
| 4: Severe | 9 (1.0) | 8 (0.8) | 5 (0.5) | 3 (0.3) | 25 (0.6) |

Synergistic Efficacy of Adapalene and BPO in the Combination Gel

Adapalene-BPO was significantly more efficacious than monotherapies and vehicle in decreasing all types of lesion counts at all time points (P<0.05; FIGS. 7A, 8A and 9A). Significant difference in total, inflammatory and non-inflammatory lesion counts reduction for adapalene-BPO was observed as early as week 1 (P<0.001). After week 4, the effect of vehicle stagnated; whereas the lesion counts in adapalene-BPO group continued to decrease throughout the study period without reaching a plateau. At week 12, the median percentage reduction from baseline in the adapalene-BPO group was 66%, 58% and 59% for IL, NIL and total lesion, respectively.

The vehicle effect was subsequently deducted and the net effect of combination and monotherapies were compared (FIGS. 7B, 8B and 9B). Adapalene-BPO treatment led to a faster decrease in all lesion counts compared to monotherapies during the entire study period. For total lesions, the net effect of adapalene-BPO at week 1 (7.4%) was greater than the sum of net effects of adapalene alone and BPO alone (1.4% plus 2.4%), indicating that the two components acted synergistically in the combination (FIG. 7B). Synergistic effect in total lesion reduction was observed at weeks 1, 2, 4 and 8. Similarly, it was observed from week 1 until week 4 for IL reduction (FIG. 8B), and until week 8 for NIL reduction (FIG. 9B).

To quantify the synergy effect, the contribution of synergy to the efficacy of adapalene-BPO was calculated. At week 1, synergy contributed to 48.7%, 62.5% and 40.9% of the efficacy of adapalene-BPO in decreasing total, IL and NIL counts, respectively (FIGS. 7C, 8C and 9C). The degree of synergy was the highest at week 1 and decreased at subsequent visits.

The significant and synergistic efficacy of adapalene-BPO was also demonstrated in the global assessment of success rate. Results of success rate began to diverge early in favor of adapalene-BPO and continued throughout the study period. At week 12, adapalene-BPO (33.1%) was superior to adapalene alone (20.0%), BPO alone (23.1%) and vehicle (14.2%) (P<0.001; FIG. 10A). In addition, the combination was significantly better than monotherapies and vehicle at week 8 (P<0.001), and better than adapalene at all time points (P<0.05).

A synergistic efficacy of adapalene and BPO in success rate was observed at weeks 1, 4, 8 and 12 (FIG. 10B). At week 1, the net effect of adapalene-BPO was entirely due to the synergy. At weeks 8 and 12, when the efficacy of adapalene-BPO was significantly superior to that of monotherapies, the contribution of synergy was 41.7% and 22.2%, respectively (FIG. 10C).

Safety Evaluation

The mean scores for dryness, erythema, scaling and stinging/burning in all treatment groups were lower than 1 (mild) at all study visits (FIGS. 11A, 11B, 11C, 11D). The scores of adapalene-BPO at week 1 were the highest among treatment groups; however, they decreased rapidly and became similar to the scores of adapalene at subsequent visits. A majority of patients in all treatment groups experienced no or only mild irritation.

The percentage of patients who experienced treatment-related AEs was higher for adapalene-BPO (21.6%) than for other groups (15.3%, 8.5% and 6.0% for adapalene, BPO and vehicle, respectively). The majority of related AEs were of dermatological nature, mild to moderate in severity, occurred early in the studies and resolved without residual effects. In adapalene-BPO group, "dry skin" occurred in 13.0% of patients and accounted for the vast majority of related AEs.

Discussion

Although several acne combination therapies are currently available, cooperative action among the individual components of those combinations have never been reported.[22-24] Therefore, the synergistic efficacy of adapalene and BPO observed in this analysis is a unique feature of the fixed-dose combination therapy. Synergy is defined as combination's effect greater than the sum of components' effect. Since the vehicle in topical acne therapies is known to be non-negligible, the vehicle effect was taken into account and the net effect of each treatment was compared.

Lesion counts change from baseline provides precise information about efficacy of the treatment. The combination therapy is superior to monotherapies and vehicle, leading to significantly greater reduction in all lesion counts at all time points (P<0.05). Adapalene-BPO demonstrated an onset of action as early as week 1, possibly explained by the highest degree of synergy observed at this time point. Such an improvement at the beginning stage of therapy may help to augment patient's confidence on the treatment and encourage adherence, which was reported to be poor in general in acne treatments.[26] Although synergy was not observed after week 8, lesion counts continued to decrease in the group of adapalene-BPO throughout the 12-week study period without stagnating, confirming the previous results of a long-term efficacy study.[16] The anti-comedogenic activity of adapalene might contribute to the observed long-lasting efficacy of the combination, since adapalene not only reduces the number of existing comedones, but also controls the development of microcomedoes and prevents the formation of new acne lesions.[5]

Compared to the change of lesion counts, the global assessment of IGA is perhaps clinically more relevant. The rapid reduction of lesion counts early during the study translated into an obvious global improvement at a later stage: The success rate of adapalene-BPO was the best numerically from week 1, increased substantially after week 4 and became significantly greater than the success rate of monotherapies and vehicle at weeks 8 and 12 (P<0.001). The synergy effect in success rate also had a longer duration than in lesion counts: At weeks 8 and 12, synergy contributed to 41.7% and 22.2% of the efficacy of adapalene-BPO respectively, explaining the striking increase of success rate in the third month of the study. Since lesion counts continued to decrease after week 12,[16] it is likely that the success rate also continues to increase after the end of the study, leading to a greater global improvement of acne. This long-lasting efficacy of the combination gel is crucial for treatment success of acne, due to the chronic nature of the disease.

Several unique features of adapalene and BPO provide potential explanations for the synergistic efficacy observed in the combination. First, both topical retinoids and BPO are keratolytic agents and may affect skin permeability by reducing the number of corneocytes layer.[27-29] Thus, the simultaneous application of adapalene and BPO may facilitate absorption and penetration of each other, leading to higher efficacy of both agents when used in combination.

Furthermore, adapalene has a unique anti-inflammatory activity.[30] The results of an in vitro study demonstrated that adapalene antagonizes the effect of *P. acnes* on inducing the expression of toll-like receptor 2,[31] which is required by the bacteria to induce the release of pro-inflammatory cytokine.[32,33] In addition, adapalene can modulate immune response by altering the expression of CD1d and IL-10,[31] thus further strengthens the antimicrobial activity of the innate immune system.

Finally, BPO possesses weak comedolytic property, in addition to its antimicrobial activity.[5] *P. acnes* induces the release of IL-1 from follicular keratinocytes,[34,35] which leads to proliferation of keratinocytes and contributes to the formation of comedones. Therefore, the activity of BPO against non-inflammatory lesions is most likely to be indirect, through its bactericidal action.

Adapalene-BPO provides synergistic efficacy without causing notable increase of irritation. The good safety profile of the combination gel demonstrated in this report is consistent with findings of previous studies.[14-21] Although the peak scores at week 1 were higher with adapalene-BPO, the overall tolerability profile of the combination was comparable to that of adapalene monotherapy at subsequent visits. The temporary increase of tolerability scores can be explained by the enhanced absorption of adapalene and BPO when applied simultaneously. However, irritation was observed mostly during the first two weeks of treatment, while the beneficial effect of synergy lasted much longer (up to 12 weeks). Furthermore, the irritation signs and dry skin condition can be easily managed by the concomitant usage of non-comedogenic moisturizers, which should be recommended when physicians prescribing acne medications.

In conclusion, the fixed-dose once-daily adapalene-BPO combination gel not only is significantly more efficacious than the corresponding monotherapies, but also provides a unique synergistic efficacy in the treatment of acne vulgaris.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

References
1. Leyden J J. A review of the use of combination therapies for the treatment of acne vulgaris. *J Am Acad Dermatol.* 2003; 49(3Suppl):S200-210.
2. Campbell J L Jr. A comparative review of the efficacy and tolerability of retinoid-containing combination regimens for the treatment of acne vulgaris. *J Drugs Dermatol.* 2007; 6(6):625-629.
3. Webster G. Mechanism-based treatment of acne vulgaris: the value of combination therapy. *J Drugs Dermatol.* 2005; 4(3):281-288.
4. Weiss J S, Shavin J S. Topical retinoid and antibiotic combination therapy for acne management. *J Drugs Dermatol.* 2004; 3(2):146-154.
5. Gollnick H, Cunliffe W, Berson D et al. Management of acne. A report from a Global Alliance to Improve Outcomes in Acne. *J Am Acad Dermatol.* 2003; 49(1 suppl): S1-S37.
6. Kligman A M, Mills O H, McGinley K J, Leyden J J. Acne therapy with tretinoin in combination with antibiotics. *Acta Dermatovener* (Stockholm). 1975; 74(Suppl):111-115.
7. Korting H C, Braun-Falco O. Efficacy and tolerability of combined topical treatment of acne vulgaris with tretinoin and erythromycin in general practice. *Drugs Exp Clin Res.* 1989; 15:447-451.
8. Zouboulis C H C, Derumeaux L, Decroix J, Maclejewska-Udziela B, Cambazards F, Stuhlert A. A multicentre, single-blind, randomized comparison of a fixed clindamycin phosphate/tretinoin gel formulation (Velac) applied once daily and a clindamycin lotion formulation (Dalacin T) applied twice daily in the topical treatment of acne vulgaris. *Br J. Dermatol.* 2000; 143:498-505.
9. Wolf J E, Kaplan D, Kraus S et al. Efficacy and tolerability of combined topical treatment of acne vulgaris with adapalene and clindamycin: a multicenter, randomized, investigator-blind study. *J Am Acad Dermatol.* 2003; 49(3 Suppl):S211-217.

10. Thielitz A, Gollnick H. Topical retinoids in acne vulgaris: update on efficacy and safety. *Am J Clin Dermatol.* 2008; 9(6):369-381.
11. Eady E A, Cove J H, Joanes D N, Cunliffe W J. Topical antibiotics for the treatment of acne vulgaris: a critical evaluation of the literature on their clinical benefit and comparative efficacy. *J Dermatol Treat.* 1990; 1:215.
12. Eady E A. Resistance to antibiotics used in dermatological practice. *Br J Dermatol.* 1998; 139:4-8.
13. Martin B, Meunier C, Montels D, Watts O. Chemical stability of adapalene and tretinoin when combined with benzoyl peroxide in presence and in absence of visible light and ultraviolet radiation. *Br J Dermatol* 1998; 139 (Suppl 52):8-11.
14. Loesche C, Pernin C, Poncet M. Adapalene 0.1% and benzoyl peroxide 2.5% as a fixed-dose combination gel is as well tolerated as the individual components alone in terms of cumulative irritancy. *Eur J. Dermatol.* 2008; 18(5):524-526.
15. Andres P, Pernin C, Poncet M. Adapalene-benzoyl perioxide once-daily, fixed-dose combination gel for the treatment of acne vulgaris: a randomized, bilateral (split-face), dose-assessment study of cutaneous tolerability in healthy participants. *Cutis.* 2008; 81:278-284.
16. Pariser D M, Westmoreland P, Morris A, Gold M H, Liu Y, Graeber M. Long-term safety and efficacy of a unique fixed-dose combination gel of adapalene 0.1% and benzoyl peroxide 2.5% for the treatment of acne vulgaris. *J Drugs Dermatol.* 2007; 6(9):899-905.
17. Brand B, Gilbert R, Baker M D et al. Cumulative irritancy comparison of adapalene gel 0.1% versus other retinoid products when applied in combination with topical antimicrobial agents. *J Am Acad Dermatol* 2003; 49(3 Suppl):S227-S232.
18. Caron D, Sorba V, Clucas A, Verschoore M. Skin tolerance of adapalene 0.1% gel in combination with other topical antiacne treatments. *J Am Acad Dermatol* 1997; 36:S113-S115.
19. Thiboutot D M, Weiss J, Bucko A et al. Adapalene-benzoyl peroxide, a fixed-dose combination for the treatment of acne vulgaris: results of a multicenter, randomized double-blind, controlled study. *J Am Acad Dermatol* 2007; 57:791-799.
20. Stein-Gold L, Tan J, Cruz-Santana A et al. Adapalene-benzoyl peroxide, a unique fixed dose combination gel for the treatment of acne: A North American, multi-center, randomized, double-blind, controlled, phase III trial in 1,668 patients. *Submitted to Cutis.*
21. Gollnick H P M, Draelos Z, Glenn M J et al. Adapalene-benzoyl peroxide, a unique fixed-dose combination topical gel for the treatment of acne vulgaris: a transatlantic, randomized, double-blind, controlled study in 1,670 patients. *Accepted by Br J. Dermatol.*
22. Lookingbill D P, Chalker D K, Lindholm J S et al. Treatment of acne with a combination clindamycin/benzoyl peroxide gel compared with clindamycin gel, benzoyl peroxide gel and vehicle gel: Combined results of two double-blind investigations. *J Am Acad Dermatol* 1997; 37:590-595.
23. Schlessinger J, Menter A, Gold M et al. Clinical safety and efficacy studies of a novel formulation combining 1.2% clindamycin phosphate and 0.025% tretinoin for the treatment of acne vulgaris. *J Drugs Dermatol.* 2007; 6(6):607-615.
24. Thiboutot D, Zaenglein A, Weiss J, Webster G, Calvarese B, Chen D. An aqueous gel fixed combination of clindamycin phosphate 1.2% and benzoyl peroxide 2.5% for the once-daily treatment of moderate to severe acne vulgaris: assessment of efficacy and safety in 2813 patients. *J Am Acad Dermatol.* 2008; 59(5):792-800.
25. Bikowski J. A new approach to comparing efficacy results from clinical trials of topical acne vulgaris treatments. *J Drugs Dermatol.* 2007; 7: 688-92.
26. Thiboutot D, Dréno B, Layton A. Acne counseling to improve adherence. *Cutis.* 2008; 81:81-86.
27. Kaidbey K H, Kligman A M, Yoshida H. Effects of intensive application of retinoic acid on human skin. *Br J Dermatol.* 1975; 92: 693-701.
28. Fulton J E Jr, Farzad-Bakshandeh A, Bradley S. Studies on the mechanism of action to topical benzoyl peroxide and vitamin A acid in acne vulgaris. *J Cutan Pathol.* 1974; 1(5):181-200.
29. Oh C W, Myung K B. An ultrastructural study of the retention hyperkeratosis of experimentally induced comedones in rabbits: the effects of three comedolytics. *J. Dermatol.* 1996; 23(3):169-80.
30. Bikowski J B. Mechanisms of the comedolytic and anti-inflammatory properties of topical retinoids. *J Drugs Dermatol.* 2005; 4(1):41-47.
31. Tenaud I, Khammari A, Dreno B. In vitro modulation of TLR-2, CD1d and IL-10 by adapalene on normal human skin and acne inflammatory lesions. *Exp Dermatol.* 2007; 16:500-6.
32. Jugeau S, Tenaud I, Knol A C et al. Induction of toll-like receptors by *Propionibacterium acnes*. *Br J. Dermatol.* 2005; 153:1105-13.
33. Kim J. Review of the innate immune response in acne vulgaris: activation of Toll-like receptor 2 in acne triggers inflammatory cytokine responses. *Dermatology.* 2005; 211:193-8.
34. Graham G M, Farrar M D, Cruse-Sawyer J E, Holland K T, Ingham E. Proinflammatory cytokine production by human keratinocytes stimulated with *Propionibacterium acnes* and *P. acnes* GroEL. *Br J Dermatol.* 2004; 150:421-8.
35. Vowels B R, Yang S, Leyden J J. Induction of proinflammatory cytokines by a soluble factor of *Propionibacterium acnes*: implications for chronic inflammatory acne. *Infect Immun.* 1995; 63:3158-65.

What is claimed is:

1. A regimen for the therapeutic treatment of acne lesions, the regimen comprising topically applying to the skin of a subject in need of said treatment, as active ingredients, 0.1% to 0.3% adapalene or a pharmaceutically acceptable salt thereof and 2.5% benzoyl peroxide, combined at fixed doses in a single formula that delivers said active ingredients together, wherein the adapalene or pharmaceutically acceptable salt thereof and the benzoyl peroxide are the only anti-acne active ingredients in said single formula, wherein the percentages of adapalene and benzoyl peroxide are percentages by weight relative to the total weight of said single formula, wherein said single formula is applied once daily for a period of 12 weeks, and wherein the net clinical benefit, expressed as success rate or reduction in total lesion counts in a group of such subjects, achieved by the single formula at week 8 is synergistic and numerically superior to the net clinical benefit achieved by the same dose of adapalene alone or of benzoyl peroxide alone at week 12.

2. The regimen of claim 1, wherein the single formula is a gel.

3. A regimen for the therapeutic treatment of acne lesions, the regimen comprising applying to the skin of a subject in need of said treatment, as active ingredients, 0.1% to 0.3% adapalene or a pharmaceutically acceptable salt thereof and 2.5% benzoyl peroxide, combined at fixed doses in a single formula that delivers said active ingredients together, wherein the adapalene or pharmaceutically acceptable salt thereof and the benzoyl peroxide are the only anti-acne active ingredients in said single formula, wherein the percentages of adapalene and benzoyl peroxide are percentages by weight relative to the total weight of said single formula, wherein said single formula is applied once daily for a period of 12 weeks, and wherein the net clinical benefit, expressed as success rate or reduction in total lesion counts in a group of such subjects, achieved by the single formula at week 1, 4 or 8 is synergistic and numerically superior to the net clinical benefit achieved by the same dose of adapalene alone or of benzoyl peroxide alone at week 4, 8 or 12, respectively.

4. The regimen of claim 3, wherein the single formula is a gel.

5. A regimen for the therapeutic treatment of acne lesions, the regimen comprising topically applying to the skin of a subject in need of said treatment, as active ingredients, 0.1% to 0.3% adapalene or a pharmaceutically acceptable salt thereof and 2.5% benzoyl peroxide, combined at fixed doses in a single formula that delivers said active ingredients together synergistically to reduce the number of non-inflammatory acne lesions by at least 40%, wherein the adapalene or pharmaceutically acceptable salt thereof and the benzoyl peroxide are the only anti-acne active ingredients in said single formula, wherein the percentages of adapalene and benzoyl peroxide are percentages by weight relative to the total weight of said single formula, wherein said single formula is applied once daily for a period of 12 weeks.

6. The regimen of claim 5, wherein the single formula is a gel.

7. A regimen for the therapeutic treatment of acne lesions, the regimen comprising applying to the skin of a subject in need of such treatment, as active ingredients, 0.1% to 0.3% adapalene or a pharmaceutically acceptable salt thereof and 2.5% benzoyl peroxide, combined at fixed doses in a single formula that delivers said active ingredients together synergistically to reduce the number of inflammatory lesions by at least 50%, wherein the adapalene or pharmaceutically acceptable salt thereof and the benzoyl peroxide are the only anti-acne active ingredients in said single formula, wherein the percentages of adapalene and benzoyl peroxide are percentages by weight relative to the total weight of said single formula, wherein said single formula is applied once daily for a period of 12 weeks.

8. The regimen of claim 7, wherein the single formula is a gel.

9. A regimen for the therapeutic treatment of acne lesions, the regimen comprising topically applying to the skin of a subject in need of said treatment, as active ingredients, 0.1% to 0.3% adapalene or a pharmaceutically acceptable salt thereof and 2.5% benzoyl peroxide, combined at fixed doses in a single formula that delivers said active ingredients together synergistically to reduce the number of total acne lesions by at least 40%, to reduce the number of non-inflammatory acne lesions by at least 40%, to reduce the number of inflammatory lesions by at least 50%, and to achieve, in a group of subjects, a degree of success of at least 20%, wherein the adapalene or pharmaceutically acceptable salt thereof and the benzoyl peroxide are the only anti-acne active ingredients in said single formula, wherein the percentages of adapalene and benzoyl peroxide are percentages by weight relative to the total weight of said single formula, wherein said single formula is applied once daily for a period of 12 weeks.

10. The regimen of claim 9, wherein the single formula is a gel.

* * * * *